(12) United States Patent
Day et al.

(10) Patent No.: US 11,390,903 B2
(45) Date of Patent: Jul. 19, 2022

(54) FULLY AUTOMATED NUCLEIC ACID EXTRACTION METHODS FOR TISSUE SAMPLES

(71) Applicant: Ventana Medical Systems, Inc., Tucson, AZ (US)

(72) Inventors: William Day, Tucson, AZ (US); Megan C. Peccarelli, Oro Valley, AZ (US)

(73) Assignee: VENTANA MEDICAL SYSTEMS, INC., Oro Valley, AZ (US)

(*) Notice: Subject to any disclaimer, the term of this patent is extended or adjusted under 35 U.S.C. 154(b) by 215 days.

(21) Appl. No.: 16/442,395

(22) Filed: Jun. 14, 2019

(65) Prior Publication Data
US 2019/0316179 A1 Oct. 17, 2019

Related U.S. Application Data

(63) Continuation of application No. PCT/US2017/067996, filed on Dec. 21, 2017.

(60) Provisional application No. 62/438,228, filed on Dec. 22, 2016.

(51) Int. Cl.
C12Q 1/6806 (2018.01)
C12N 15/10 (2006.01)

(52) U.S. Cl.
CPC ....... *C12Q 1/6806* (2013.01); *C12N 15/1003* (2013.01)

(58) Field of Classification Search
CPC .............................. C12Q 1/68; C12N 15/1003
See application file for complete search history.

(56) References Cited

U.S. PATENT DOCUMENTS

| | | | | |
|---|---|---|---|---|
| 6,180,778 B1* | 1/2001 | Bastian | ............... | C12N 15/1006 536/25.3 |
| 6,982,168 B1* | 1/2006 | Topalian | ............... | C12N 15/85 435/384 |
| 10,295,540 B1* | 5/2019 | Buturovic | ............... | G16B 40/00 |
| 2002/0028159 A1* | 3/2002 | Lebl | ............... | C40B 50/14 422/533 |
| 2002/0172950 A1* | 11/2002 | Kenny | ............... | C12Q 1/682 435/6.11 |
| 2004/0242495 A1* | 12/2004 | Staines | ............... | C12N 5/0619 514/23 |
| 2006/0040283 A1* | 2/2006 | Xiang | ............... | C12Q 1/6841 435/91.2 |
| 2013/0203072 A1 | 8/2013 | Tian et al. | | |
| 2020/0325524 A1* | 10/2020 | Handique | ............... | F16K 99/0001 |

FOREIGN PATENT DOCUMENTS

| | | |
|---|---|---|
| JP | 2014045689 A | 3/2014 |
| WO | 2001046402 A1 | 6/2001 |
| WO | 2002042737 A2 | 5/2002 |
| WO | 2006130632 A2 | 12/2006 |
| WO | 2011025442 A1 | 3/2011 |
| WO | 2013057050 A1 | 4/2013 |
| WO | 2013074885 A1 | 5/2013 |
| WO | 2014052551 A1 | 4/2014 |
| WO | 2016004548 A1 | 1/2016 |

OTHER PUBLICATIONS

Kashofer et al., Quality Control of RNA Preservation and Extraction from Paraffin-Embedded Tissue: Implications for RT-PCR and Microarray Analysis. PLOS One 8(7) : e70714 (Year: 2013).*
Ludyga et al., Nucleic acids from long-term preserved FFPE tissues are suitable for downstream analyses. Virchows Arch 460: 131 (Year: 2012).*
Moorthie et al., Review of massively parallel DNA sequencing technologies. HUGO J. 5 : 1-12 (Year: 2011).*
Ripoli et al., A Comparison of Fresh Frozen vs. Formalin-Fixed, Paraffin-Embedded Specimens of Canine Mammary Tumors via Branched-DNA Assay. Intl. J of Molecular Sciences 17 :723, pp. 1-11 (May 2016) (Year: 2016).*
Shi et al., DNA Extraction from Archival Formalin-fixed, Paraffin-embedded Tissue Sections Based on the Antigen Retrieval Principle: Heating Under the Influence of pH. J. of Histochemistry & Cytochemistry 50(8) : 1005 (Year: 2002).*
Shi et al., Antigen Retrieval Immunohistochemistry: Review and Future Prospects in Research and Diagnosis over Two Decades. J. of Histochemistry & Cytochemistry 50(8) : 1005 (Year: 2011).*
Trejo et al., Extraction-free whole transcriptome gene expression analysis of FFPE sections and histology-directed subareas of tissue. PLOS one 14 (2) : e0212031, 22 pgs (Year: 2019).*
Turashvili et al., Nucleic acid quantity and quality from paraffin blocks: Defining optimal fixation, processing and DNA/RNA extraction techniques. Experimental and Molecular Pathology 92 : 33-43 (Year: 2012).*
Wang et al., RNA-Seq: a revolutionary tool for transcriptomics. Nature Reviews |Genetics 10 :57 (Year: 2009).*
Bagasra, O. Protocols for the in situ PCR-amplification and detection of mRNA and DNA sequences. Nature Protocols 2(11) : 2782-2795 (Year: 2007).*
Bagasra, O., Protocols for the insitu PCR-amplification and mRNA detection of mRNA and DNA sequences. Nature Protocols 2(11) : 2782 (Year: 2007).*
Emmert-Buck et al., Laser Capture Microdissection. Science 274 : 998 (Year: 1996).*

(Continued)

*Primary Examiner* — Ethan C Whisenant
(74) *Attorney, Agent, or Firm* — Eric Grant Lee; Kellie L. Carden

(57) ABSTRACT

Automated methods for extracting nucleic acid from one or more tissue samples disposed on slides are disclosed. The methods utilize an automated slide staining apparatus that dispenses a plurality of nucleic acid extraction reagents onto the tissue sample, thus creating an extracted nucleic acid sample. The extracted nucleic acid sample may be used directly in downstream applications such as nucleic acid amplification or sequencing procedures, or may be further purified.

59 Claims, 7 Drawing Sheets
(1 of 7 Drawing Sheet(s) Filed in Color)

(56) References Cited

OTHER PUBLICATIONS

Zhuang et al., A microdissection technique for archival DNA analysis of Specific Cell Populations in lesions <1mm in size. American J. of Pathology 146(3) : 620 (Year: 1995).*

International Search Report and Written Opinion dated Mar. 28, 2018 in connection with PCT/US2017067996 filed Dec. 21, 2017, pp. 1-13.

Nara Yoon, "Analysis of HER2 status in breast carcinoma by fully automated HER2 fluorescence in situ hybridization (FISH): comparison of two immunohistochemical tests and manual FISH", US National Library of Medicine National Institutes of Health, Dec. 20, 2013, 755-760, 122(9), WO.

Tubbs, et al, Appl Immunohistochem Mol Morphol. Automation of Manuel Components and Image Quantification of Direct Dual Label, 2006, pp. 436-440, vol. 14 No. 4.

* cited by examiner

Superior DNA Extraction Efficiency using the Automated Extraction Method on H&E Stained Slides Superior DNA Extraction Efficiency using the Automated Extraction Method on Microdissected Slides

FULLY AUTOMATED NUCLEIC ACID EXTRACTION METHODS FOR TISSUE SAMPLES

CROSS-REFERENCE TO RELATED APPLICATIONS

This patent application is a continuation of International Patent Application No. PCT/US2017/067996 filed Dec. 21, 2017, which claims priority to and the benefit of U.S. Provisional Application No. 62/438,228 filed Dec. 22, 2016. Each of the above patent applications is incorporated herein by reference as if set forth in its entirety.

FIELD OF THE INVENTION

This present invention relates to nucleic acid extraction methods for tissue samples, more particularly to automated methods for extracting nucleic acids, e.g., DNA, RNA, from tissue samples such as tissue samples mounted on slides, including but not limited to tissue samples used for histochemical staining or other staining (e.g., immunohistochemistry, in situ hybridization, hematoxylin and eosin staining (H&E), or the like.

BACKGROUND OF THE INVENTION

Immunohistochemistry (IHC) refers to the processes of detecting, localizing, and/or quantifying antigens, such as a protein, in a biological sample using specific binding moieties, such as antibodies specific to the particular antigens. IHC provides the substantial advantage of identifying exactly where a particular protein is located within the tissue sample. It is also an effective way to examine the tissues themselves. In situ hybridization (ISH) refers to the process of detecting, localizing, and quantifying nucleic acids. Both IHC and ISH can be performed on various biological samples, such as tissue (e.g. fresh frozen, formalin-fixed paraffin-embedded (FFPE)) and cytological samples. Recognition of the targets can be detected using various labels (e.g., chromogenic, fluorescent, luminescent, radiometric, etc.).

Nucleic acid sequence analysis of cancer patient tissue samples provides new insights useful to guide therapies and augment understanding of this heterogeneous and complicated disease. The success of molecular studies utilizing formalin-fixed paraffin-embedded (FFPE) tissue is dependent on both the quantity and quality of the DNA and/or RNA extracted. An obstacle encountered in archival and current analysis has been extraction of nucleic acids from FFPE tissues widely used to diagnose disease. Extraction of nucleic acids from FFPE tissue is typically laborious and difficult, and there is little or no standardization to the extraction process. Isolation of the nucleic acids often involves scraping the tissue sample from the slide into a tube (e.g., an Eppendorf tube) and isolating and purifying the nucleic acids using currently known manual methods (e.g., commercially available kits). These methods have several drawbacks. For example, often there is a need to deparaffinize the sample, and there is a risk of sample loss during the scraping process. Sample loss is particularly problematic with small or rare samples. Further, commercially available kits are costly, manual, and time consuming, often requiring overnight enzymatic digestion. In addition, commercially available manual nucleic acid extraction kits often require the use hazardous chemicals (e.g., xylene for deparaffinization) and require further purification of the nucleic acid before it can be further utilized in other downstream applications.

SUMMARY OF INVENTION

It was surprisingly discovered that nucleic acid could be extracted from FFPE tissue samples on an automated staining machine. The extraction procedure takes place entirely on the instrument. Further, the extraction can be completed in just a few hours (e.g., just over two hours). All steps are automated; thus, there is no hands-on time for users (which also helps reduce variability and error during the extraction), and there is no chemical exposure to the user. Because of the widespread use of FFPE samples, the nucleic acid extraction methods of the present invention can be used for a majority of anatomic pathology samples. Further advantages include the ability to extract nucleic acids for retrospective studies and the ability to extract nucleic acids from samples used previously for histochemistry (e.g., immunohistochemistry, in situ hybridization), staining (e.g., H&E, etc.), and the like. The methods of the present invention may be used on stained slides. In some embodiments, the methods of the present invention may be used on unstained slides. In addition, multiple slides can be used at the same time, e.g., 30 slides at one time.

The methods feature a deparaffinization step, an antigen retrieval step, a protease treatment step, and an elution step (e.g., a heat step) for eluting DNA or RNA from the tissue. In some embodiments, the methods (e.g., RNA extraction methods) also feature an additional treatment step featuring guanidine thiocyanate or an equivalent reagent. Without wishing to limit the present invention to any theory or mechanism, it is surprising that an antigen retrieval step, which is typically used just during immunohistochemistry (IHC) procedures, is beneficial for automated nucleic acid extraction.

The automated nucleic acid extraction methods described herein provide improved sample quality and comparable to better sample yield than on-market kits. Analysis of extracted nucleic acid indicates that DNA and RNA extracted by the automated method herein are far less degraded than samples extracted using on-market methods. The automated extraction methods herein also have potential to be useful in cases of limited tissue availability. Many tissue samples are subjected to tissue staining and there is not enough excess tissue to perform molecular analysis. The automated methods herein have demonstrated utility to efficiently recover DNA from previously stained tissue, thus allowing users the unique opportunity to stain a single tissue section and perform molecular analysis on the same section, eliminating the need for excess tissue.

Nucleic acid extracted using the automated methods described herein is suitable for a variety of downstream applications. For example, DNA extracted using the automated methods herein may be a usable template for PCR based analysis, gel analysis, and sequencing. RNA extracted using the automated methods herein may be useful for gel analysis, cDNA synthesis, subsequent PCR, sequencing, etc.

In one aspect, the present invention features an automated method for extracting nucleic acid from one or more tissue samples (e.g., fresh, frozen, FFPE tissue samples, etc.) disposed on slides. The method utilizes an automated slide stainer to automatically dispense a plurality of nucleic acid extraction reagents to the one or more tissue samples to treat the one or more tissue samples, respectively, in a predetermined sequence such that said reagents come into contact with the one or more tissue samples on the one or more slides. The method further comprises treating the one or more samples with said reagents, thereby resulting in one or more extracted nucleic acid samples comprising extracted nucleic acid.

In an additional aspect, the method further comprises removing the one or more extracted nucleic samples from the one or more slides (e.g., into a tube or other vessel). The method may further comprise purifying and/or analyzing the nucleic acid from one or more extracted nucleic acid samples. In some embodiments, the analyzing may comprise amplification of the extracted nucleic acid sample, sequencing of the extracted nucleic acid sample, a combination thereof, etc.

In some embodiments, the extracted nucleic acid is DNA. In some embodiments, the extracted nucleic acid is RNA. In some embodiments, the nucleic acid extraction reagents are selected from the group consisting of deparaffinization solutions, buffers, detergents, surfactants, proteases, salts, enzymes, and alcohols. In some embodiments, the tissue samples are fresh, frozen, formalin fixed or paraffin embedded (FFPE). In some embodiments, the sample is a liquid cytology sample. In some embodiments, the one or more tissue samples are stained.

As previously discussed, in some embodiments, the method comprises subjecting the sample or samples to a deparaffinization step (e.g., treating the sample or samples with a deparaffinization solution, a buffer, etc.). In some embodiments, the method comprises subjecting the sample or samples to an antigen retrieval (e.g., treating the sample or samples with an antigen retrieval solution, a buffer, etc.). In some embodiments, the method comprises subjecting the sample or samples to a protease treatment step (e.g., treating the sample or samples with a protease, an enzyme, etc.). In some embodiments, the method comprises subjecting the sample or samples to an elution step (e.g., treating the sample or samples with heat).

In some embodiments, the methods feature cutting away undesired tissue prior to the aforementioned steps (e.g., deparaffinization step, antigen retrieval step, etc.).

In some embodiments, the extracted nucleic acid is from 10 to 500 bp. In some embodiments, the extracted nucleic acid is from 50 to 500 bp. In some embodiments, the extracted nucleic acid is from 100 to 1000 bp. In some embodiments, the extracted nucleic acid is from 100 to 2000 bp. In some embodiments, the extracted nucleic acid is from 10 to 3000 bp. In some embodiments, the extracted nucleic acid greater than 3,000 bpd in length.

The present invention features an automated method for extracting nucleic acid (e.g., DNA, RNA) from tissue samples disposed on one or more slides. In some embodiments, the methods comprises, in an automated staining machine, treating the samples on the one or more slides with a deparaffinization reagent; treating the samples on the one or more slides with an antigen retrieval buffer; treating the samples on the one or more slides with a protease buffer; and heating the samples on the one or more slides to yield an eluate, wherein the eluate comprises isolated nucleic acid from the respective sample.

In some embodiments, the method further comprises removing the eluate from the samples on the one or more slides. In some embodiments, the method further comprises purifying the isolated nucleic acid. In some embodiments, the method further comprises performing nucleic acid amplification on the isolated nucleic acid. In some embodiments, the method further comprises analyzing the isolated nucleic acid. In some embodiments, the analyzing comprises sequencing. In some embodiments, the method further comprises treating the samples on the one or more slides with guanidine thiocyanate after the samples on the one or more slides are treated with the protease.

In some embodiments, the samples on the one or more slides are FFPE samples, fresh samples, or frozen samples. In some embodiments, the samples are microdissected samples. In some embodiments, the samples on the one or more slides are unstained samples. In some embodiments, the samples on the one or more slides are stained samples. In some embodiments, the stained samples are samples stained with H&E or an immunohistochemistry dye or an in situ hybridization dye.

In some embodiments, the automated staining machine comprises one or more dispensers for dispensing the deparaffinization reagent, antigen retrieval buffer, and protease onto the samples on the one or more slides. In some embodiments, the automated staining machine further comprises a heating element for heating the samples on the one or more slides.

The present invention features an automated method for extracting RNA from tissue samples disposed on one or more slides. In some embodiments, the methods comprises, in an automated staining machine, treating the samples on the one or more slides with a deparaffinization reagent; treating the samples on the one or more slides with an antigen retrieval buffer; treating the samples on the one or more slides with a protease; treating the samples on the one or more slides with guanidine thiocyanate; and heating the samples on the one or more slides to yield an eluate, wherein the eluate comprises isolated nucleic acid from the respective sample.

In some embodiments, the method further comprises removing the eluate from the samples on the one or more slides. In some embodiments, the method further comprises purifying the isolated nucleic acid. In some embodiments, the method further comprises performing nucleic acid amplification on the isolated nucleic acid. In some embodiments, the method further comprises analyzing the isolated nucleic acid. In some embodiments, the analyzing comprises sequencing.

In some embodiments, the samples on the one or more slides are FFPE samples, fresh samples, or frozen samples. In some embodiments, the samples are microdissected samples. In some embodiments, the samples on the one or more slides are unstained samples. In some embodiments, the samples on the one or more slides are stained samples. In some embodiments, the stained samples are samples stained with H&E or an immunohistochemistry dye or an in situ hybridization dye.

The present invention also features an automated method for extracting nucleic acid (e.g., DNA, RNA) from tissue samples disposed on one or more slides. The method may comprise receiving the one or more slides comprising one or more tissue samples in an automated slide staining apparatus, wherein the automated slide staining apparatus is configured to automatically dispense a plurality of nucleic acid extraction reagents to the one or more tissue samples to treat the one or more tissue samples, respectively; dispensing said reagents in a predetermined sequence such that said reagents come into contact with the one or more tissue samples on the one or more slides; and treating the one or more samples with said reagents, thereby resulting in one or more extracted nucleic acid samples comprising extracted nucleic acid.

In some embodiments, the method further comprises removing the one or more extracted nucleic samples from the one or more slides. In some embodiments, the method further comprises purifying the nucleic acid from one or more extracted nucleic acid samples. In some embodiments, the method further comprises analyzing the nucleic acid from one or more extracted nucleic acid samples. In some embodiments, the analyzing comprises performing nucleic acid amplification. In some embodiments, the analyzing comprises nucleic acid sequencing.

In some embodiments, the nucleic acid extraction reagents are selected from the group consisting of deparaffinization solutions, buffers, detergents, surfactants, proteases, salts, enzymes and alcohols. In some embodiments, the one or more tissue samples are fresh, frozen, formalin fixed or paraffin embedded. In some embodiments, the one or more tissue samples are stained.

The present invention also features methods for isolating nucleic acid (e.g., DNA, RNA) from a sample on a slide. In some embodiments, the method comprises placing the sample on the slide on an automated staining machine; and running an extraction protocol on the automated staining machine. In some embodiments, the method comprises placing the sample on the slide on a dissection instrument; dissecting the sample on the slide to remove unwanted tissue; placing the sample on the slide on an automated staining machine; and running an extraction protocol on the automated staining machine. The extraction protocol instructs the automated staining machine to dispense reagents in a predetermined sequence such that said reagents come into contact with the sample on the slide, thereby resulting in an eluate on the sample on the slide comprising an isolated nucleic acid sample comprising isolated nucleic acid.

In some embodiments, the method further comprises removing the eluate on the sample on the slide. In some embodiments, the method further comprises purifying the isolated nucleic acid. In some embodiments, the method further comprises comprising performing nucleic acid amplification on the isolated nucleic acid. In some embodiments, the method further comprises analyzing the isolated nucleic acid. In some embodiments, the analyzing comprises sequencing. In some embodiments, the reagents include guanidine thiocyanate. In some embodiments, the samples are FFPE samples, fresh samples, or frozen samples. In some embodiments, the samples are unstained samples. In some embodiments, the samples are stained samples. In some embodiments, the stained samples are samples stained with H&E or an immunohistochemistry dye or an in situ hybridization dye.

The present invention also features kits for nucleic acid extraction on automated staining machines. The kits may comprise any of the reagents disclosed herein or combinations thereof. For example, the kit may comprise a deparaffinization buffer, an antigen retrieval buffer, and a protease treatment buffer. The kit may further comprise an elution buffer. The kit may further comprise a guanidine thiocyanate treatment reagent.

The present invention also provides workflow methods, e.g., methods for processing and preparing a tissue section from a tumor of a patient and extracting DNA from the sample as described herein. For example, the method may comprise preparing tissue section from a tumor of a patient, e.g., sectioning a FFPE tissue sample of a tumor of a patient using a microtome; mounting the tissue section on a slide; and utilizing an automated slide stainer to automatically dispense a plurality of nucleic acid extraction reagents to the tissue section resulting in an extracted nucleic acid samples comprising extracted nucleic acid.

The present invention also provides automated staining machines for performing the methods herein. The present invention also provides an automated staining machine comprising a memory coupled to a processor, wherein the memory stores computer-readable instructions that, when executed by the processor, cause the automated staining machine to perform operations for a method according to the present invention.

The present invention also provides an automated system comprising a slide holder, reagents, and dispensers for performing a method according to the present invention. In some embodiments, the system comprises memory coupled to a processor, wherein the memory stores computer-readable instructions that, when executed by the processor, cause the automated system to perform operations for a method herein. In some embodiments, the dispensers are adapted to dispense reagents onto a slide in the slide holder.

The present invention also provides workflow methods. In some embodiments, the method comprise preparing a tissue section from a tissue of a patient on a slide; applying method according to the present invention to the tissue section, wherein the method is for extracting nucleic acid. In some embodiments, the tissue of the patient is a tumor tissue.

The present invention also provides an automated system for purifying nucleic acid. In some embodiments, the system comprises an automated machine for accepting samples, wherein the automated machine executes a method according to the present invention, wherein the method purifies nucleic acid.

The present invention also provides an automated system for analyzing nucleic acid. In some embodiments, the system comprises an automated machine for accepting samples, wherein the automated machine executes a method according to the present invention, wherein the method purifies nucleic acid; wherein the automated machine further executes a method for analyzing the purified nucleic acid. In some embodiments, the method for analyzing the nucleic acid comprises amplifying the nucleic acid. In some embodiments, the method for analyzing the nucleic acid comprises sequencing the nucleic acid.

The present invention also provides an automated system for amplifying nucleic acid. In some embodiments, the system comprises an automated machine for accepting samples, wherein the automated machine executes a method according to the present invention, wherein the method purifies nucleic acid; wherein the automated machine further executes a method for amplifying the purified nucleic acid.

The present invention also provides an automated system for sequencing nucleic acid. In some embodiments, the system comprises an automated machine for accepting samples, wherein the automated machine executes a method according to the present invention, wherein the method purifies nucleic acid; wherein the automated machine further executes a method for sequencing the purified nucleic acid.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF PREFERRED EMBODIMENTS

Definitions

Figure 1:
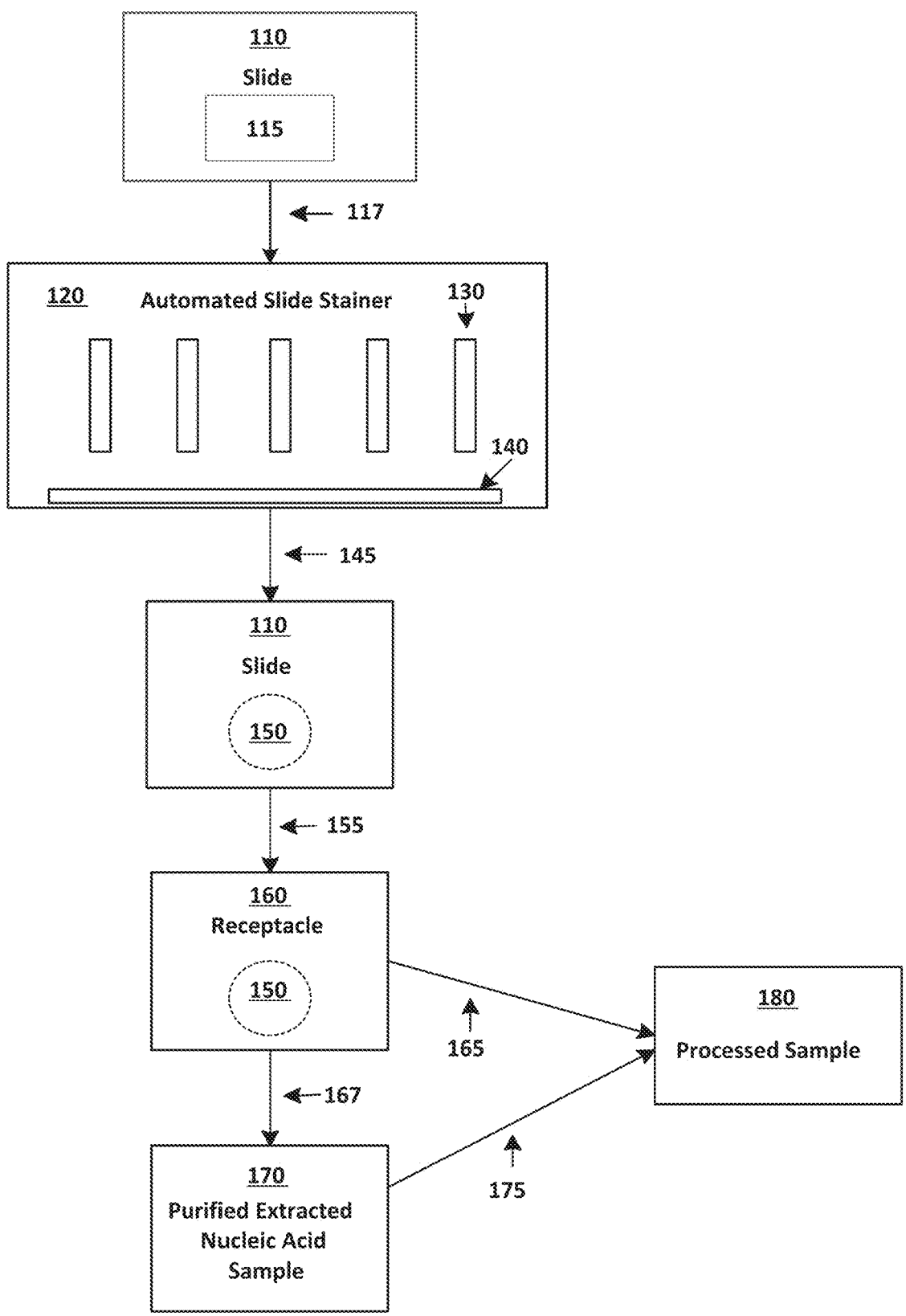
FIG. 1 shows a flowchart illustrating an embodiment of the nucleic acid extraction methods of the present invention.

As used herein, the terms "sample" and "biological sample" shall refer to any composition containing or presumed to contain a biomarker or a composition being tested for the presence or absence of a particular biomarker. Samples may include purified or separated components of cells, tissues, or blood, e.g., DNA, RNA, proteins, cell-free portions, or cell lysates. The sample can be a formalin-fixed, paraffin-embedded (FFPE) tissue sample, e.g., from a tumor or metastatic lesion, e.g., primary tumor or metastatic tumor. The sample can also be from previously frozen or fresh tissue, or from a liquid sample, e.g., blood or a blood component (plasma or serum), urine, semen, saliva, sputum, mucus, semen, tear, lymph, cerebral spinal fluid, material washed from a swab, etc. Samples also may include constituents and components of in vitro cultures of cells obtained from an individual, including cell lines. The sample can also be partially processed from a sample directly obtained from an individual, e.g., cell lysate or blood depleted of red blood cells.

As used herein, the term "tissue sample" shall refer to a cellular sample that preserves the cross-sectional spatial relationship between the cells as they existed within the subject from which the sample was obtained. "Tissue sample" shall encompass both primary tissue samples (i.e. cells and tissues produced by the subject) and xenografts (i.e. foreign cellular samples implanted into a subject).

As used herein, "histochemical detection" refers to a process involving labeling a biomarker or other structures in a tissue sample with detection reagents in a manner that permits microscopic detection of the biomarker or other structures in the context of the cross-sectional relationship between the structures of the tissue sample. Examples include affinity histochemistry (AHC), immunohistochemistry (IHC), chromogenic in situ hybridization (CISH), fluorescent in situ hybridization (FISH), silver in situ hybridization (SISH), and H&E staining of formalin-fixed, paraffin-embedded tissue sections.

As used herein, the term "section" shall refer to a thin slice of a tissue sample suitable for microscopic analysis, typically cut using a microtome. When used as a verb, the term "section" refers to making a section of a tissue sample, typically using a microtome.

As used herein, the term "subject" refers to any multicellular vertebrate organism, such as human or non-human mammals (e.g., veterinary subjects).

As used herein, the term "nucleic acid" includes DNA (deoxyribonucleic acid) and RNA (ribonucleic acid).

When used as a noun, the term "stain" shall refer to any substance that can be used to visualize specific molecules or structures in a cellular sample for microscopic analysis, including bright field microscopy, fluorescent microscopy, electron microscopy, and the like. When used as a verb, the term "stain" shall refer to any process that results in deposition of a stain on a cellular sample (e.g., tissue sample, cytological sample, etc.).

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

DESCRIPTION OF THE INVENTION

The present invention features automated methods for extracting nucleic acid from one or more tissue samples disposed on slides. The methods utilize an automated slide staining apparatus, which dispenses a plurality of reagents onto the tissue sample to generate an extracted nucleic acid sample. The extracted nucleic acid sample may be used in various downstream applications including but not limited to nucleic acid amplification, sequencing procedures, further purification, etc.

Compared to commercially available kits, the extractions of the present invention can be completed much faster. For example, for multiple slides (e.g., about 30 slides), the nucleic acid methods can be completed in about 2.5 hours with a hands-on time requirement of about 5 minutes to place the slides on an instrument, start the instrument, and pipette off the eluted nucleic acid when the instrument has finished the extraction process. A FFPE DNA isolation kit (for processing multiple slides, e.g., about 24 slides) takes about 5 hours with a hands-on time requirement of about 2.6 hours for deparaffinization, pipetting lysis buffer and proteinase K, vortexing, spinning, removing tubes, pipetting more buffers or isopropanol, column purification, and elution. For the present invention, the reduction in time needed, including the reduction in hands-on time needed, helps reduce labor costs, reduces errors, improves standardization, and improves turn around time for samples. The methods of the present invention also improve safety by eliminating the exposure of lab personnel to harmful chemicals often used in commercially available kits or traditional methods.

Briefly, the present invention features automated methods for extracting nucleic acid from one or more tissue samples (e.g., fresh, frozen, FFPE tissue samples, liquid cytology samples, etc.) disposed on slides. The methods utilizes an automated slide stainer to automatically dispense a plurality of reagents to the one or more tissue samples to treat the one or more tissue samples, respectively, in a predetermined sequence such that said reagents come into contact with the one or more tissue samples on the one or more slides. The method further comprises treating the one or more samples with said reagents, thereby resulting in one or more extracted nucleic acid samples comprising extracted nucleic acid. The methods may further comprise removing the one or more extracted nucleic samples from the one or more slides (e.g., into a tube or other vessel).

Automated Staining Machines

The methods of the present invention are performed on an automated staining machine (slide stainer) or other appropriate automated slide processing machine. Specific examples of automated staining machines (e.g., IHC/ISH slide stainers) include: itelliPATH (Biocare Medical), WAVE (Celerus Diagnostics), DAKO OMNIS and DAKO AUTOSTAINER LINK 48 (Agilent Technologies), BENCHMARK XT (Ventana Medical Systems, Inc.), BENCHMARK ULTRA (Ventana Medical Systems, Inc.), BENCHMARK GX (Ventana Medical Systems, Inc.), VENTANA H&E 600 (Ventana Medical Systems, Inc.), BENCHMARK Special Stains (Ventana Medical Systems, Inc.), DISCOVERY XT (Ventana Medical Systems, Inc.), VENTANA DISCOVERY ULTRA (Ventana Medical Systems, Inc.), Leica BOND, and Lab Vision Autostainer (Thermo Scientific). Automated staining machines (automated slide stainers) are also described by Prichard, Overview of Automated Immunohistochemistry, Arch Pathol Lab Med., Vol. 138, pp. 1578-1582 (2014), incorporated herein by reference in its entirety. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. The methods of the present invention may be adapted to be performed on any appropriate automated staining machine (or automated slide processing machine).

Automated slide stainers typically include at least a stainer unit for dispensing a reagent to implement staining protocols onto a slide. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BENCHMARK and VENTANA DISCOVERY instruments); (3) capillary gap staining, in which the slide surface is placed in proximity parallel to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In some variations of capillary gap staining, the reagents are mixed in the gap, such as translating gap technology, in which a gap is created between the slide and a curved surface and movement of the surfaces relative to one another effects mixing (see U.S. Pat. No. 7,820,381, assigned to Ventana Medical Systems, Inc.); and dynamic gap staining, which uses capillary forces similar to capillary gap staining to apply sample to the slide, and then translates the parallel surfaces relative to one another to agitate the reagents during incubation to effect reagent mixing (such as the staining principles implemented on DAKO OMNIS slide stainers (Agilent)). It has recently been proposed to use inkjet technology to deposit reagents on slides. See PCT Publication No. WO 2016-170008 A1, assigned to Ventana Medical Systems, Inc.

As an example, the VENTANA DISCOVERY ULTRA instrument features slide drawers with 30 independent slide reaction chambers with dedicated bulk reagent supply lines and individual slide heaters, a reagent carousel with 35 reagent positions, and the ability to hold up to 7 different bulk reagents in 3- to 6-liter onboard containers. The system has a slide temperature range from ambient temperature up to about 100° C. The VENTANA BENCHMARK Special Stains instrument has a slide carousel for processing up to 20 slides with independent temperature control for each position, a reagent carousel with 25 reagents positions, and the ability to hold up to 4 bulk solutions in 3- to 6-liter onboard containers. The BENCHMARK ULTRA instrument can process up to 30 slides with independent processing/functionality and temperature control for each position. The system has a reagent carousel with 35 reagent positions and the ability to hold up to 7 different bulk reagents, which can be changed without process interruption. The system has a slide temperature range from ambient temperature up to about 100° C.

This list of staining principles and staining machines is not intended to be exhaustive, and the present methods and systems are intended to include any staining technology and system (both known and to be developed in the future) that can be used to apply the appropriate reagents to the sample.

Samples

Samples used in the methods of the present invention are tissue samples on slides. The tissue samples may be of any type appropriate for histological examination on an automated staining machine (as described herein). For example, the tissue sample may comprise a biopsy or surgical resection. The tissue sample may further comprise a section of cancerous or healthy tissue. The tissue sample may be taken from a liquid cytology sample.

Samples may be processed and adhered to the slide. The processing steps involved depend on the type of analysis planned. For example, the tissue sample may be fresh, frozen, formalin fixed paraffin embedded (FFPE), etc. In some embodiments, the tissue sample is fixed in order to preserve the shape of the cells or tissue. Common fixatives include formaldehyde, ethanol, methanol, and/or picric acid. Pieces of tissue may be embedded in paraffin wax to increase their mechanical strength and stability and to make them easier to cut into thin slices.

The tissue samples may then be mounted to the slide. Mounting usually involves attaching the samples to a microscope slide for observation and analysis. In some embodiments, cells may be grown directly on a slide. For samples of loose cells (as with a blood smear or a pap smear), the sample can be directly applied to a slide. For other type of samples, thin sections (slices) are made using a microtome; these slices can then be mounted using methods known to one of skill in the art.

In one embodiment, the tissue samples may be unstained. In other embodiments, the tissue samples are stained before the nucleic acid isolation method of the present invention is performed. For example, the sample may be immersed (before or after fixation and mounting) in dye solution, followed by rinsing and observation. Additionally, the dyes may be deposited onto the samples mounted on the slide. Such stains may include, for example, haematoxylin and eosin stains, stains for histochemistry (e.g., immunohistochemical stains and in situ hybridization stains), as well as other types of stains. These and other types of tissue stains and staining techniques are well known to one of skill in the art. The stained slides may then be analyzed by methods well known in the art, for example with a microscope or through digital scanning.

Microdissection of FFPE tissue is often used for molecular analysis of a specific region of interest. In some embodiments, the tissue samples of the present invention are microdissected samples, e.g., one or more sections of the tissue may be have been microdissected away or segregated to leave only the tissue or region of interest on the slide. The one or more portions that are segregated or dissected away from the tissue sample may be generated using methods known to one of skill in the art. For example, tissue dissection in the clinical molecular diagnostics laboratory is often performed by manually scraping tissue (via scalpel or razor blade) directly off standard glass slides. Laser capture microdissection (LCM) instrumentation or the AVENIO Millisect tissue dissection system (Roche Molecular Systems, Pleasanton, Calif.) may be sued for tissue microdissection. In some embodiments, images from a stained and mounted tissue section (for example, an H&E section) are pre-marked to identify areas of interest (e.g., tumor cells), then used to guide dissection using the instrument software on the dissection instrument to remove the areas of non-interest (e.g., non-cancerous sections) of the tissue. The remaining adhered tissue sections, representing the tissue of interest, may then undergo the automated nucleic acid extraction process as presently disclosed. The methods of the present invention therefore allow for nucleic acid extraction from smaller tissue section as compared to current manual methods.

In some embodiments, the methods of the present invention are effective in extracting nucleic acids from a single 4 to 10 micron tissue sample. The majority of current manual methods require an eight to ten micron section, or multiple sections pooled into a single sample. Because of the small sample size, the current method also allows for extraction of sections containing rare or infrequently occurring genes. The method is also useful when very small amounts of tissue are available for analysis.

Overview of Automated Extraction Method

FIG. 1 illustrates a non-limiting embodiment of the automated nucleic acid extraction method (100) of the present invention. For example, the method features the use of one or more slides (110) with one or more tissue samples (115).

Referring to arrow (117) in FIG. 1, the automated nucleic acid extraction method (100) is implemented on an automated staining machine (120) (e.g., an IHC/ISH slide stainer) or other automated slide processing system comprising at least one unit for dispensing a reagent. Automated staining machines in general are described above. This list of staining principles is not intended to be exhaustive, and the present methods and systems are intended to include any staining technology (both known and to be developed in the future) that can be used to apply the appropriate reagents to the sample.

If the sample (115) is a sample embedded in paraffin, the sample (115) can be deparaffinized with the automated staining machine (120) using appropriate deparaffinizing fluid(s). After the waste remover removes the deparaffinizing fluid(s), any number of substances can be successively applied to the sample (115). The substances can be for pretreatment, cell lysis, denaturation, washing or the like.

The automated staining machine (120) can apply a wide range of nucleic extraction reagents (130) to the sample. The reagents (130) may include, without limitation, buffers, detergents, surfactants, proteases, salts, enzymes and alcohols. The reagents (130) can be fluids (e.g., gases, liquids, or gas/liquid mixtures), or the like. The reagents (130) can be solutions (e.g., aqueous solutions or other types of solutions), or the like. In some embodiments, the reagents (130) include those used in deparaffinization of embedded tissue samples. Such reagents may include, for example, xylene and alcohols. These reagents are toxic and are regulated as hazardous chemicals. Since the methods of the present invention are automated and performed on the automated staining machine (120), the current method greatly reduces the chemical exposure risk typically associated with deparaffinization and nucleic acid extraction from FFPE tissues.

In some embodiments, the automated slide stainer (120) may include one or more heating or cooling elements (140). In one example, these elements (140) are used to raise or lower the temperature of the slide (110) containing the one or more tissue samples (115), as is known to one of skill in the art.

Referring again to FIG. 1, the automated slide staining apparatus (120) is configured to automatically dispense a plurality of nucleic acid extraction reagents (130) to the one or more tissue samples (115) to treat the one or more tissue samples (115), respectively. As described previously, such nucleic acid extraction reagents (130) act to extract the nucleic acid from the tissue sample (115). As indicated by arrow (145), treatment of the sample (115) with the extraction reagents (130) results in a slide (110) containing an extracted nucleic acid sample (150).

As indicated by arrow (155), in some embodiments, the extracted nucleic acid sample (150) is removed from the slide (110) and placed into a receptacle (160), for instance an Eppendorf tube or test tube. The removal of the extracted sample (150) may be accomplished by methods known to one of skill in the art, e.g., by pipetting, or by automated methods. Referring to arrow (165), after removal, the extracted nucleic acid sample (150) may then be utilized in further downstream processes, for instance by nucleic acid amplification techniques or sequencing techniques, resulting in a processed extracted nucleic acid sample (180).

Referring to arrow (167), in some embodiments, the extracted sample (150) may be further purified by methods known in the art, resulting in a purified extracted nucleic acid sample (170). Such purification methods may include, for example, extraction purification (e.g., phenol-chloroform extraction), column purification, magnetic bead purification and electrophoresis purification, etc. Referring to arrow (175), the purified extracted nucleic sample (170) may then be utilized in further downstream processes, for instance by nucleic acid amplification techniques or sequencing techniques, resulting in a processed extracted nucleic acid sample (180).

The populations of nucleic acid fragments collected by the currently described automated method 100 are longer than fragments collected by current manual methods. Longer fragments are beneficial for sequencing applications as well as studies investigating single nucleotide polymorphisms, alternative splicing, exon-exon boundaries, or copy number variation. The majority of DNA fragments collected using the automated method (100) are more than 1500 base pairs in length. These fragments can be used immediately for downstream application such as PCR without the need for purification; however, as illustrated in FIG. 1, samples can be purified if desired.

In some embodiments, the extracted nucleic acid is from 10 to 500 bp. In some embodiments, the extracted nucleic acid is from 50 to 500 bp. In some embodiments, the extracted nucleic acid is from 100 to 1000 bp. In some embodiments, the extracted nucleic acid is from 100 to 2000 bp. In some embodiments, the extracted nucleic acid is from 10 to 3000 bp. In some embodiments, the extracted nucleic acid is from 1500 to 3000 bp. In some embodiments, the extracted nucleic acid is at least 500 bp in length. In some embodiments, the extracted nucleic acid is at least 1500 bp in length. In some embodiments, the extracted nucleic acid greater than 3,000 bp in length.

In some embodiments, the eluate (volume of solution comprising the extracted nucleic acid yielded from the elution step) is from 20 µl to 100 µl. In some embodiments, the eluate is from 100 µl to 500 µl. In some embodiments, the eluate is from 50 µl to 500 µl. In some embodiments, the eluate is from 100 µl to 800 µl. In some embodiments, the eluate is from 50 µl to 1 ml.

DNA Extraction Method

The DNA extraction methods herein comprise a deparaffinization step, an antigen retrieval step, a protease treatment step, and an elution step (e.g., a heat step).

For example, the sample may be incubated in the automated staining machine at a particular temperature (or range or combination of temperatures) for a length of time with a deparaffinization buffer. The deparaffinization buffer comprises a reagent for paraffin removal from tissue samples. The sample is then incubated in the automated staining machine at a particular temperature (or range or combination of temperatures) for a length of time with an antigen retrieval buffer. Antigen retrieval buffers are well known to one of ordinary skill in the art. The sample is then incubated in the automated staining machine at a particular temperature (or range or combination of temperatures) for a length of time with a protease treatment solution. The protease treatment solution comprises a reagent or protease for enzymatic digestion of sections of FFPE tissue. Proteases are well known to one of ordinary skill in the art (e.g., endopeptidases, e.g., trypsin, pepsin, etc.). The elution step comprises incubating the sample in an elution buffer in the automated staining machine at a particular temperature (or range or combination of temperatures) for a length of time. Following the elution step, the puddle on the sample is removed (pipetted). The sample contains the extracted DNA.

The deparaffinization treatment step may be performed at a first temperature from 55° C. to 65° C. (e.g., 55° C., 56° C., 57° C., 58° C., 59° C., 60° C., 61° C., 62° C., 63° C., 64° C., 65° C., etc.) for a length of time followed by a second temperature from 70° C. to 80° C. (e.g., 70° C., 71° C., 72° C., 73° C., 74° C., 75° C., 76° C., 77° C., 78° C., 79° C., 80° C., etc.) for a length of time. The antigen retrieval step may be performed at a temperature from 90° C. to 100° C. (e.g., 90° C., 91° C., 92° C., 93° C., 94° C., 95° C., 96° C., 97° C., 98° C., 99° C., 100° C., etc.) for a length of time from 25 to 45 minutes (e.g., 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, etc.). The protease treatment step may be performed at a temperature from 35° C. to 40° C. (e.g., 35° C., 36° C., 37° C., 38° C., 39° C., 40° C., etc.) for a length of time from 15 to 45 minutes (e.g., 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, etc.). The elution step may be performed at a temperature from 90° C. to 100° C. (e.g., 90° C., 91° C., 92° C., 93° C., 94° C., 95° C., 96° C., 97° C., 98° C., 99° C., 100° C., etc.) for a length of time from 15 to 25 minutes (e.g., 15 minutes, 16 minutes, 17 minutes, 18 minutes, 19 minutes, 20 minutes, 21 minutes, 22 minutes, 23 minutes, 24 minutes, 25 minutes, etc.). The present invention is not limited to the aforementioned temperatures or times of treatment.

As previously discussed, the nucleic acid extracted using the automated methods described herein is suitable for a variety of downstream applications. For example, DNA extracted using the automated methods herein has been demonstrated to be a usable template for PCR based analysis, gel analysis, and sequencing.

RNA Extraction Method

The RNA extraction methods herein comprise a deparaffinization step, an antigen retrieval step, a protease treatment step, a guanidine thiocyanate step, and an elution step (e.g., a heat step). The guanidine thiocyanate step may comprise guanidine thiocyanate or an equivalent reagent.

For example, the sample may be incubated in the automated staining machine at a particular temperature (or range or combination of temperatures) for a length of time with a deparaffinization buffer. The deparaffinization buffer comprises a reagent for paraffin removal from tissue samples. The sample is then incubated in the automated staining machine at a particular temperature (or range or combination of temperatures) for a length of time with an antigen retrieval buffer. Antigen retrieval buffers are well known to one ordinary skill in the art. The sample is then incubated in the automated staining machine at a particular temperature (or range or combination of temperatures) for a length of time with a protease treatment solution. The protease treatment solution comprises a reagent or protease for enzymatic digestion of sections of FFPE tissue. Proteases are well known to one of ordinary skill in the art (e.g., endopeptidases, e.g., trypsin, pepsin, etc.). The guanidine thiocyanate step comprises incubating the sample in the automated staining machine at a particular temperature (or range or combination of temperatures) for a length of time with guanidine thiocyanate (or equivalent). The elution step comprises incubating the sample in an elution buffer in the automated staining machine at a particular temperature (or range or combination of temperatures) for a length of time. Following the elution step, the puddle on the sample is removed (pipetted). The sample contains the extracted RNA.

The deparaffinization treatment step may be performed at a first temperature from 55° C. to 65° C. (e.g., 55° C., 56° C., 57° C., 58° C., 59° C., 60° C., 61° C., 62° C., 63° C., 64° C., 65° C., etc.) for a length of time followed by a second temperature from 70° C. to 80° C. (e.g., 70° C., 71° C., 72° C., 73° C., 74° C., 75° C., 76° C., 77° C., 78° C., 79° C., 80° C., etc.) for a length of time. The antigen retrieval step may be performed at a temperature from 90° C. to 100° C. (e.g., 90° C., 91° C., 92° C., 93° C., 94° C., 95° C., 96° C., 97° C., 98° C., 99° C., 100° C., etc.) for a length of time from 25 to 45 minutes (e.g., 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, etc.). The protease treatment step may be performed at a temperature from 35° C. to 40° C. (e.g., 35° C., 36° C., 37° C., 38° C., 39° C., 40° C., etc.) for a length of time from 15 to 45 minutes (e.g., 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, etc.). The guanidine thiocyanate step may be performed at a temperature from 35° C. to 40° C. (e.g., 35° C., 36° C., 37° C., 38° C., 39° C., 40° C., etc.) for a length of time from 10 to 25 minutes (e.g., 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, etc.). The elution step may be performed at a temperature from 90° C. to 100° C. (e.g., 90° C., 91° C., 92° C., 93° C., 94° C., 95° C., 96° C., 97° C., 98° C., 99° C., 100° C., etc.) for a length of time from 15 to 25 minutes (e.g., 15 minutes, 16 minutes, 17 minutes, 18 minutes, 19 minutes, 20 minutes, 21 minutes, 22 minutes, 23 minutes, 24 minutes, 25 minutes, etc.). The present invention is not limited to the aforementioned temperatures or times of treatment.

As previously discussed, the nucleic acid extracted using the automated methods described herein is suitable for a variety of downstream applications. For example, RNA extracted using the automated methods herein may be useful for gel analysis, cDNA synthesis and subsequent PCR, as well as sequencing or other applications.

Example 1: Analysis of Extraction Methods

Example 1 describes an analysis of extraction methods according to the present invention. The present invention is not limited to the protocols or reagents in this example.

Manual extraction of nucleic acids from tissue, particularly FFPE tissue, is a laborious and difficult process. Manual methods have a number of limitations. For example, the reagents can be costly and the extraction protocols may be long, often requiring overnight enzymatic digestion. Manual workflow can also increases the likelihood of human errors. As described herein, the automated methods of the present invention eliminate much of the manual manipulation of the sample and decrease the amount of reagents needed for deparaffinization and nucleic acid extraction. In addition, elimination of the manual steps decreases the extraction time. The methods of the present invention also provide samples that are of better quality than manual methods, and the methods of the present invention are also comparable (or better than) manual methods with respect to DNA extraction efficiency.

In order to determine the extraction efficiency of the automated methods of the present invention, DNA yield from the automated method of the present invention was compared to DNA yield from an on-market DNA extraction kit for FFPE tissue. DNA was extracted from unstained samples, H&E stained samples, immunohistochemistry stained samples, and microdissected samples. Extraction efficiency varied depending on the sample type; however, the automated method of the present invention demonstrated equivalent or better performance across all sample types tested.

In one study, DNA was extracted from serial, four-micron tissue sections of unstained colon, breast, liver, and prostate. DNA extracted using the automated method was suspended in about 500 µl of buffer. DNA extracted using the manual kit was eluted off the purification column in 50 µl of elution buffer then diluted with buffer to a total volume of 500 µl. DNA samples were then subjected to real-time PCR analysis for three DNA amplicons of varying length: ACTB, GAPDH, and 18s (see Table 1).

TABLE 1

| Amplicon | Amplicon Length | Use |
| --- | --- | --- |
| ACTB | 139 | gDNA Amplification |
| GAPDH | 58 | gDNA Amplification |
| 18S | 187 | gDNA Amplification |
| ACTB | 171 | cDNA Amplification |

TABLE 1-continued

| Amplicon Length | | |
|---|---|---|
| Amplicon | Amplicon Length | Use |
| GAPDH | 122 | cDNA Amplification |
| GUSB | 81 | cDNA Amplification |

The average cycle threshold (Ct) values using the automated method of the present invention, as well as the on-market manual method are shown below in Table 2.

TABLE 2

| Average Cycle Threshold (Ct) | | | | |
|---|---|---|---|---|
| DNA Extraction Method | Tissue | Average Ct Value (ACTB) | Average Ct Value (GAPDH) | Average Ct Value (18S) |
| On-market Kit | Colon | 30.76 | 28.78 | 28.71 |
| Automated Method | Colon | 29.47 | 27.59 | 25.97 |
| On-market Kit | Breast | 33.95 | 31.84 | 29.43 |
| Automated Method | Breast | 30.42 | 29.67 | 27.05 |
| On-Market Kit | Liver | 29.41 | 27.97 | 25.57 |
| Automated Method | Liver | 28.72 | 27.76 | 24.95 |
| On-market Kit | Prostate | 29.29 | 27.76 | 26.27 |
| Automated Method | Prostate | 28.59 | 26.82 | 24.95 |

All of the Ct values are lower for the automated method than the on-market manual method, indicating that the automated samples were amplified with greater efficiency. Statistical analysis of the relative copy numbers shows that the automated method has equal to greater yield than the on-market method (data not shown). For the breast tissue, the automated method outperformed the on-market kit for all three amplicons tested. There was no statistically significant difference in extraction efficiency for any of the amplicons tested using lung tissue. For colon and prostate, the automated method's efficiency was deemed equivalent or better, but appeared to be amplicon-dependent. This study demonstrates the robustness of the automated, demonstrating that DNA can be efficiently isolated from many clinically relevant tissue types.

Figure 2:
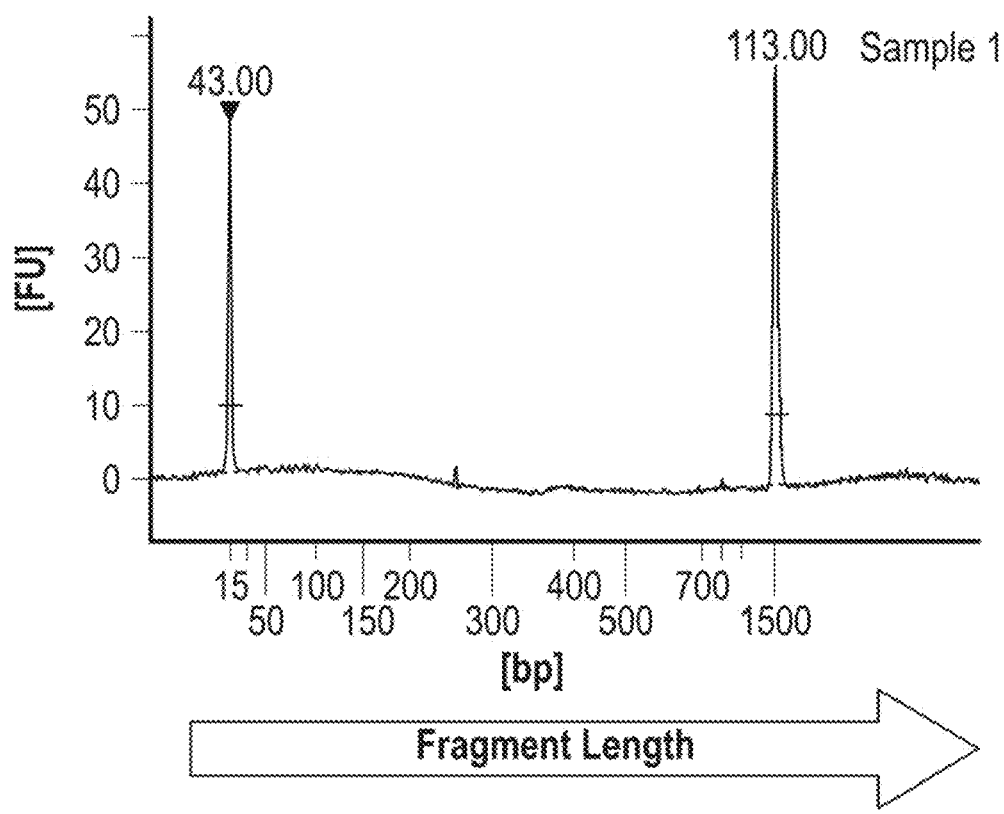
FIG. 2 shows fragment lengths of DNA extracted from unstained slides using either an on-market FFPE DNA extraction kit or the automated methods of the present invention. Graphs are representative electropherograms of purified DNA extracted by the respective method. Samples were tissue sections of fixed tonsil. All samples were from the same tissue block and serial slide sections were used. Samples were column purified prior to analysis. Longer DNA fragments were extracted from slides using the methods of the present invention.
Figure 2:
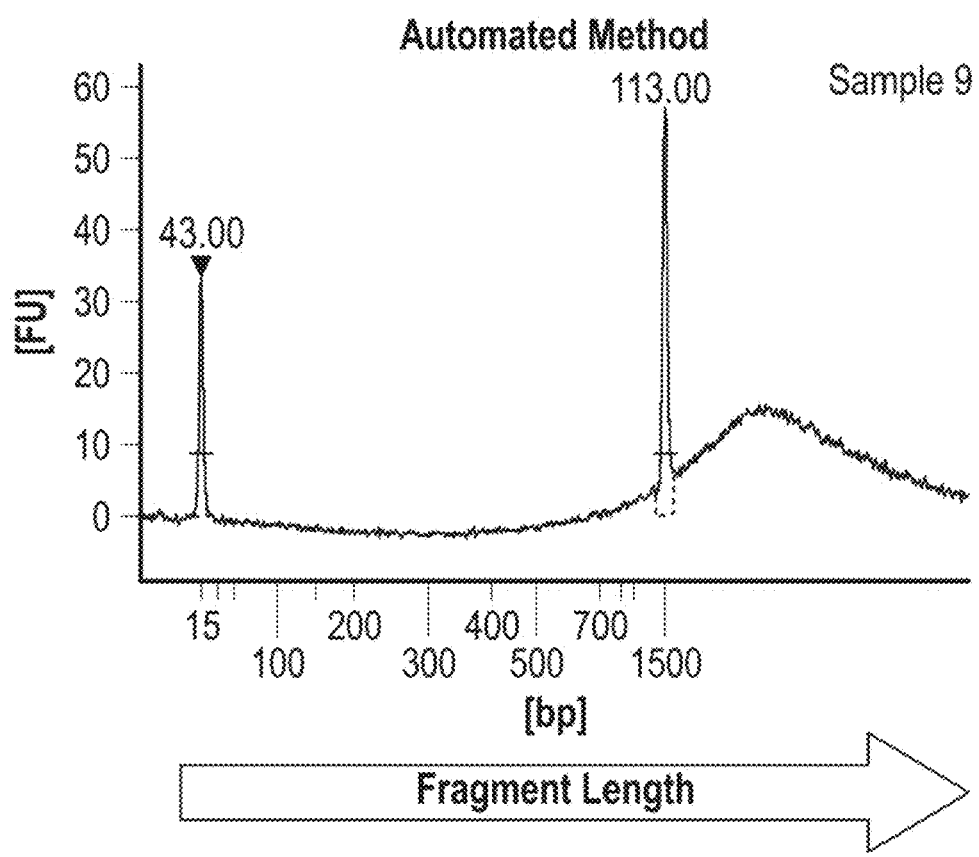

In another study, DNA was extracted from four-micron sections of tonsil. The population of DNA fragments extracted from tonsil using the fully automated method and the on-market kit were evaluated by bioanalyzer analysis. The electrograms showed that the average DNA fragment length varies greatly between the two methods (the populations of nucleic acid fragments collected by the automated methods of the present invention are longer than fragments collected by on-market manual methods. The majority of the fragments extracted using the on-market method are less than 300 bp in length (see FIG. 2, top panel). In contrast, the majority of the DNA fragments extracted with the fully automated method are longer than 1500 bp (see FIG. 2, bottom panel). Longer fragments may enable greater efficiency for PCR-based tests and be beneficial for other downstream applications, e.g., sequencing applications, studies investigating single nucleotide polymorphisms, alternative splicing, exon-exon boundaries, or copy number variation. As previously discussed, fragments collected by the methods of the present invention can be used immediately for downstream application without the need for purification; however, samples can be purified if desired.

Figure 3A:
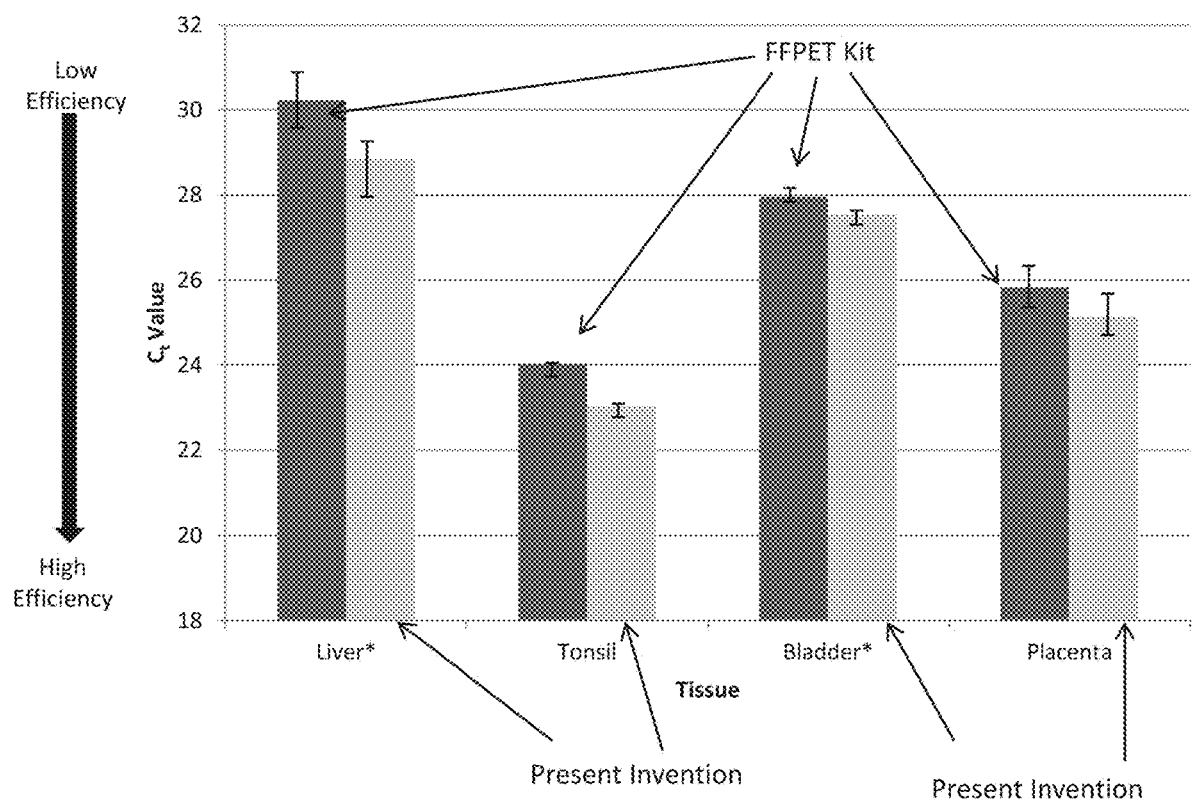
FIG. 3A shows a comparison of DNA extraction efficiency (for GAPDH) between an on-market FFPE DNA extraction kit and the extraction methods of the present invention. Samples included liver samples (tumor and normal samples), tonsil samples, bladder samples (tumor and normal samples), and placenta samples. Liver samples were 6 months old. Tonsil samples were 7 months old. Bladder samples were 21 months old. Placenta samples were 10 months old. Samples were unstained. Error bars represent standard error of difference. The extraction methods of the present invention showed equivalent (or greater) efficiency.
Figure 3B:
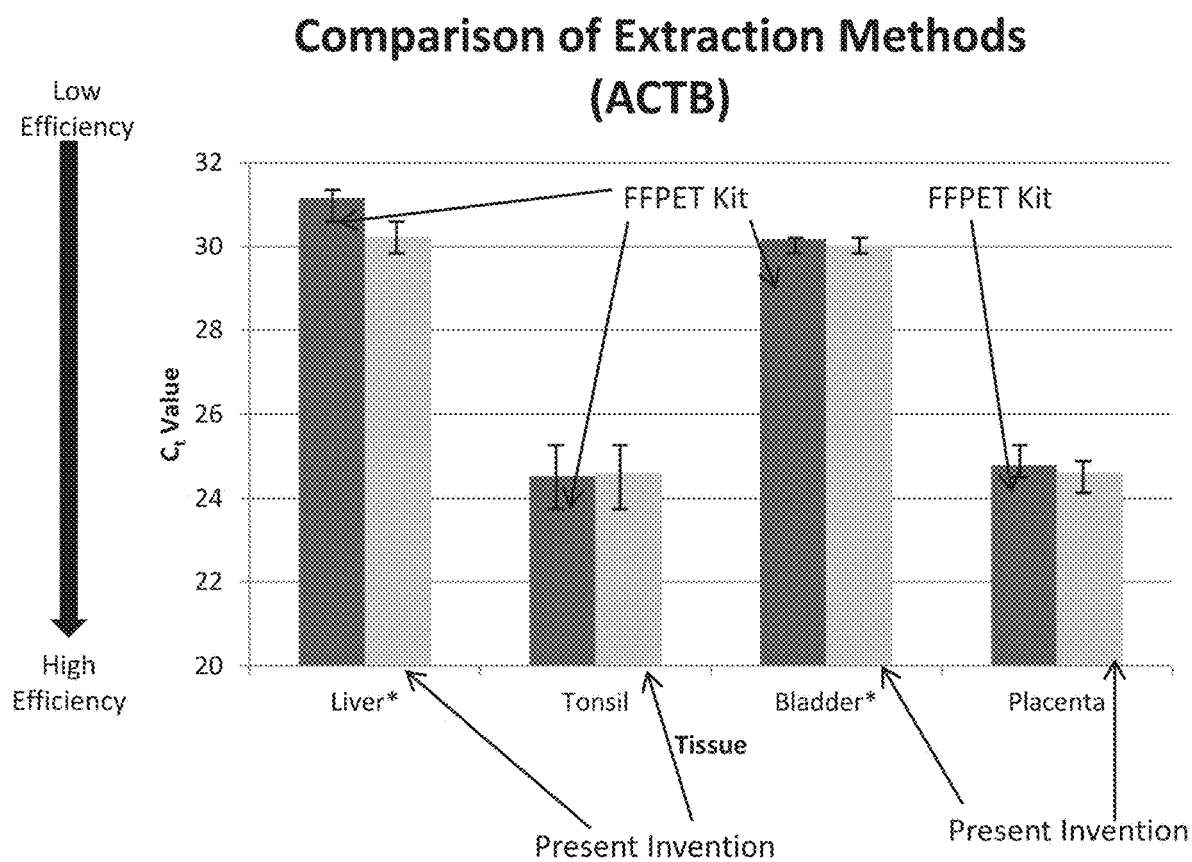
FIG. 3B shows a comparison of DNA extraction efficiency (for ACTB) between an on-market FFPE DNA extraction kit and the extraction methods of the present invention. Samples included liver samples (tumor and normal samples), tonsil samples, bladder samples (tumor and normal samples), and placenta samples. Liver samples were 6 months old. Tonsil samples were 7 months old. Bladder samples were 21 months old. Placenta samples were 10 months old. Samples were unstained. Error bars represent standard error of difference. The extraction methods of the present invention showed equivalent (or greater) efficiency.
Figure 3C:
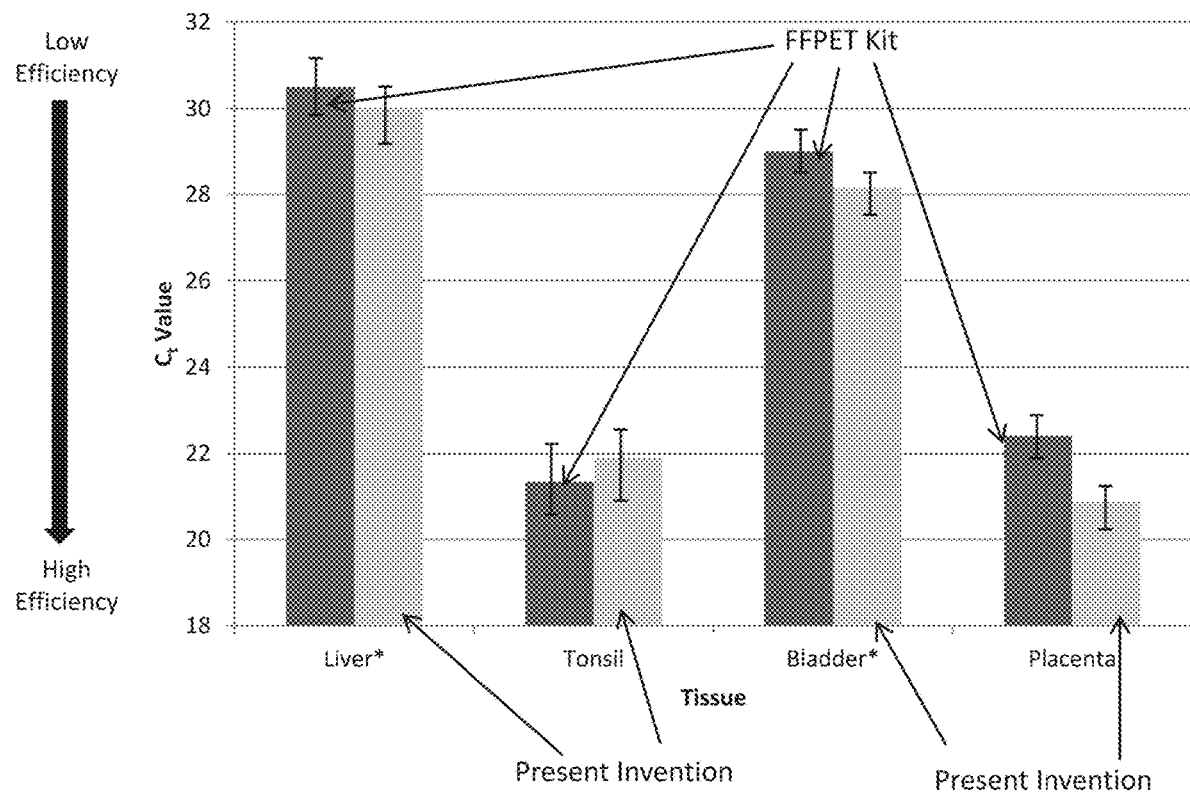
FIG. 3C shows a comparison of DNA extraction efficiency (for 18s rRNA) between an on-market FFPE DNA extraction kit and the extraction methods of the present invention. Samples included liver samples (tumor and normal samples), tonsil samples, bladder samples (tumor and normal samples), and placenta samples. Liver samples were 6 months old. Tonsil samples were 7 months old. Bladder samples were 21 months old. Placenta samples were 10 months old. Samples were unstained. Error bars represent standard error of difference. The extraction methods of the present invention showed equivalent (or greater) efficiency.

FIG. 3A, FIG. 3B, and FIG. 3C shows comparisons of DNA extraction efficiency (for GAPDH, ACTB, and 18s, respectively) between an on-market FFPE DNA extraction kit and the extraction methods of the present invention. Samples were unstained and included liver samples (tumor and normal samples), tonsil samples, bladder samples (tumor and normal samples), and placenta samples. As shown in FIG. 3A, the extraction methods of the present invention showed equivalent or greater efficiency for GAPDH extraction in the liver, tonsil, bladder, and placenta samples used. As shown in FIG. 3B, the extraction methods of the present invention showed equivalent or greater efficiency for ACTB extraction in the liver, bladder, and placenta samples used. As shown in FIG. 3C, the extraction methods of the present invention showed equivalent or greater efficiency for 18S extraction in the liver, bladder, and placenta samples used.

In many cases, molecular analysis of FFPE tissue is not feasible due to lack of tissue availability. Small tissue samples and microbiopsies yield very few tissue sections, most of which are reserved for tissue staining. The automated methods of the present invention are able to extract DNA from previously stained tissue sections, providing an opportunity for molecular analysis of samples with limited tissue. The use of stained tissues also provides users the unique opportunity to perform staining and molecular analysis on the same tissue section, instead of comparing different tissue sections.

In another study to test the DNA extraction efficiency from stained tissue, serial sections (4 µM thickness) of FFPE tonsil were subject to H&E staining or subject to immunohistochemistry (IHC) staining with 3,3'-Diaminobenzidine (DAB) for Cytokeratin 8 and 18 expression. DNA was extracted from the H&E and IHC stained tissue using both the automated extraction method and the manual kit. DNA samples extracted using the on-market kit were diluted as described above.

Real-time PCR analysis of ACTB, GAPDH, and 18s revealed that the automated method recovers significantly more DNA from stained tissue than the on-market kit. Ct values for both methods are shown below in Table 3.

TABLE 3

| Average Cycle Threshold (Ct) | | | | |
|---|---|---|---|---|
| DNA Extraction Method | Stain | Average Ct Value (ACTB) | Average Ct Value (GAPDH) | Average Ct Value (18S) |
| On-market Kit | H&E | 30.94 | 31.75 | 27.99 |
| Automated Method | H&E | 23.14 | 23.09 | 19.70 |
| On-market Kit | DAB | 26.58 | 26.81 | 22.58 |
| Automated Method | DAB | 24.25 | 24.22 | 19.93 |

For two of the three amplicons, there is a statistically significant difference in amplification efficiency when using the automated method compared to the on-market kit (p value for ACTB=0.0397, p value for GAPDH: 0.0025, p value for 18s: 0.1602). Although there was not a statistically significant difference observed with 18s, there is a notable difference in Ct values that suggests greater extraction efficiency from the automated method.

Figure 4:
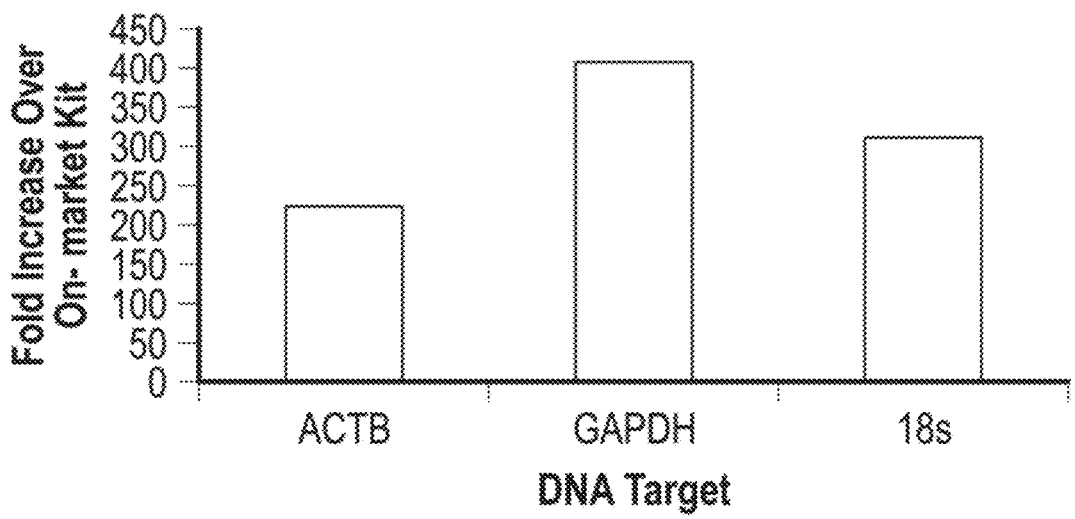
FIG. 4 shows DNA extraction efficiency using the automated methods of the present invention as compared to the on-market kit (in fold increase). The samples used were H&E stained slides (4-micron tissue sections).
Figure 5:
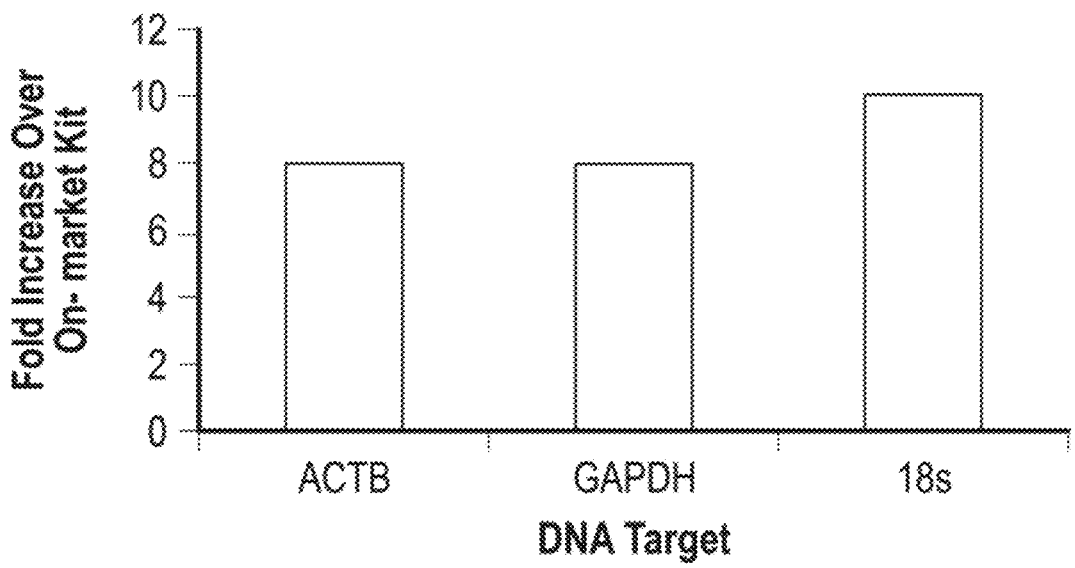
FIG. 5 shows the DNA extraction efficiency of slides microdissected with AVENIO Millisect (Roche Molecular Systems, Pleasanton, Calif.) using the automated extraction methods of the present invention as compared to the on-market kit (shown in fold increase over the on-market kit). The methods of the present invention outperform the on-market kit.

For IHC, the average Ct values using the automated method were lower than the average Ct values using the on-market kit (see Table 3). For all three amplicons, there is a statistically significant difference in amplification efficiency when using the automated method compared to the on-market kit (p value for ACTB=0.342, p value for GAPDH: 0.0163, p value for 18s: 0.0241). In summary, the automated method outperforms the on-market kit, and recovers 200-400 fold more DNA from H&E stained tissues (see FIG. 4) and 8-10 fold more DNA from IHC stained tissues (see FIG. 5).

Figure 6:
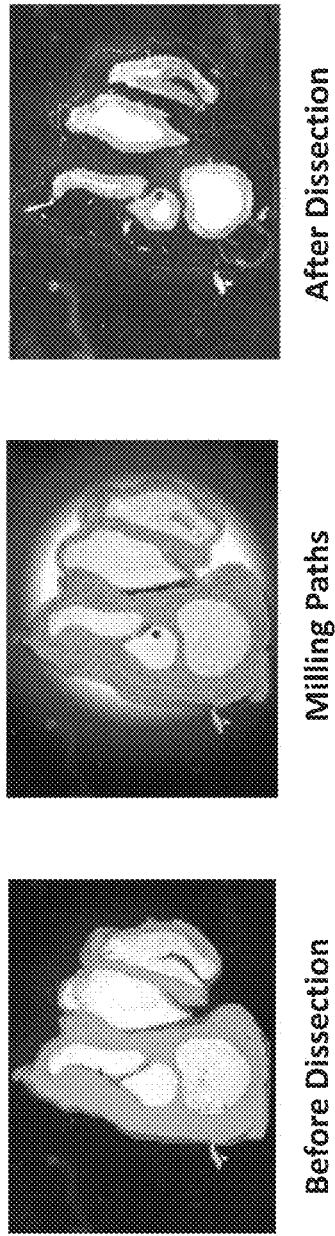
FIG. 6 shows images of a 4 micron sample before microdissection with AVENIO Millisect (Roche Molecular Systems, Pleasanton, Calif.) and after microdissection (and milling path of the instrument) (the dissection that was completed for the example in FIG. 5). In the image of the tissue section after microdissection, the white areas indicate tissue left on the slide.

Microdissection may be paired with the automated extraction methods of the present invention. Removal of unwanted tissue leaves the tissue regions of interest on the slide, allowing nucleic acid extraction from only the regions of interest, thus, enriching the sample. In one study, the AVENIO MilliSect (Roche Molecular Systems, Pleasanton, Calif.) was used to dissect tissue sections (see FIG. 6). Tonsil was used as a model to simulate tumor and normal. Clusters of germinal centers were left on the slide as the regions of interest. The mantle zone of the tonsil was removed.

After dissection, slides containing tissue regions of interest were subject to DNA extraction via the automated method of the present invention and the on-market manual kit. Samples extracted from the on-market kit were diluted as described above. After extraction, qPCR analysis was performed on all samples. Amplicons used in the qPCR analysis included ACTB, GAPDH, and 18S. As shown in Table 4, the Ct values for the automated method were much lower for all three amplicons than the Ct values for the on-market kit. These results indicate that more DNA was recovered from the dissected samples by the automated method.

TABLE 4

Average Cycle Threshold (Ct)

| DNA Extraction Method | Average Ct Value (ACTB) | Average Ct Value (GAPDH) | Average Ct Value (18S) |
| --- | --- | --- | --- |
| On-market Kit | 31.35 | 31.97 | 28.78 |
| Automated Method | 23.36 | 23.88 | 18.68 |

DNA extracted by the automated method was successfully used in a number of downstream applications. In the studies described above, the DNA was directly subject to qPCR after extraction without the need for purification. The elution buffer in which the DNA is suspended did not produce a signal or amplify a PCR product (data not shown), eliminating the need for purification for this particular use. Purified DNA samples were used in bioanalyzer analysis as previously described.

DNA extracted from both stained and unstained slides was also used successfully in sequencing applications. After extraction, the samples underwent buffer exchange using the KAPA Pure Bead Cleanup (KAPA Biosystems Inc.). Importantly, sequencing analysis indicates that DNA extracted from stained slides can be successfully used for sequencing applications. Additionally, samples extracted using the automated method demonstrate greater uniformity of coverage compared to samples extracted using an on-market kit.

Figure 7:
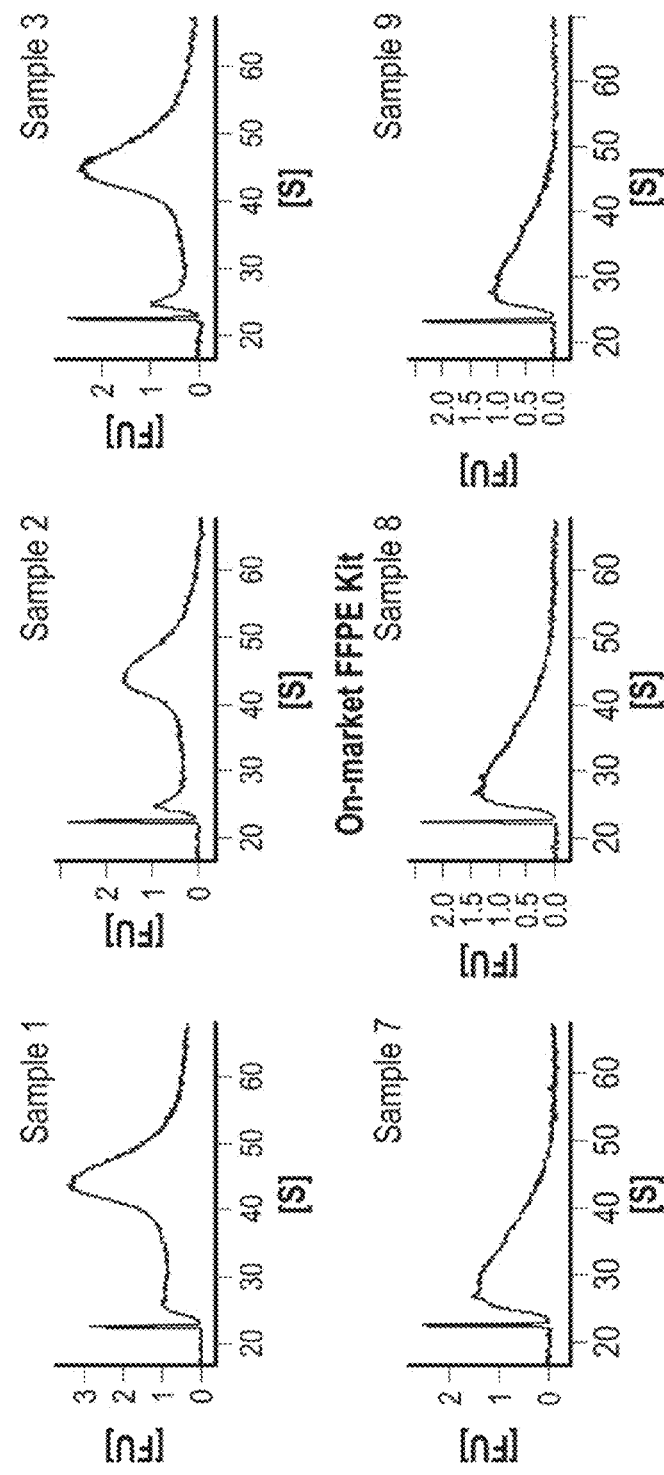
FIG. 7 shows a comparison of quality of RNA extracted using the automated methods of the present invention and the on-market FFPE DNA extraction kit. Graphs are representative electropherograms of purified RNA extracted by the respective method. Note all concentrations are normalized and all samples are from the same tissue block, and serial slide sections were used. The RNA extracted using the methods of the present invention are of higher quality.

The automated extraction method may be used for RNA extraction from FFPE tissues. Referring to FIG. 7, the quality of the RNA extraction via the automated method was compared to RNA extracted by an on-market FFPE RNA extraction kit. The RNA extracted from the automated method was column purified after removal of the sample from the instrument. Following purification, RNA was run on the Bioanalyzer. Bioanalyzer analysis of extracted RNA indicated that RNA extracted by the automated method is far less fragmented than RNA extracted using the on-market kit (FIG. 7). Longer RNA transcripts may be desirable for many downstream applications including PCR-based approaches and some RNA-seq.

All RNA extracted by the automated method was column purified. After purification, the RNA was subject to a number of downstream applications. First, the RNA was used directly in bioanalyzer analysis. The RNA was also successfully used as a template for cDNA synthesis, and the cDNA was subject to qPCR.

Example 2: DNA Extraction Protocol

Example 2 describes an example of a protocol scheme for automated DNA extraction on unstained tissue. The present invention is not limited to the protocol in this example.
DNA Extraction Scheme for Automated Slide Stainer (Steps 2-5 are Performed on the Automated Slide Staining Instrument)
 1. Slides Placed on Instrument
 2. Deparaffinization
 3. Antigen Retrieval
 4. Protease Treatment
 5. Heat Elution
 6. User pipettes liquid off slide (liquid contains extracted DNA)

Example 3: RNA Extraction Protocol

Example 3 describes an example of a protocol for automated RNA extraction on unstained tissue. The present invention is not limited to the protocol in this example.
RNA Extraction Scheme for Automated Slide Stainer (Steps 2-6 are Performed on the Automated Slide Staining Instrument)
 1. Slides Placed on Instrument
 2. Deparaffinization
 3. Antigen Retrieval
 4. Protease Treatment
 5. Guanidine Thiocyanate Treatment
 6. Heat Elution
 7. User pipettes liquid off slide (liquid contains extracted RNA)

The automated RNA extraction method described herein provides improvements compared to manual technologies. This automated method can extract RNA from thirty samples in less than three hours, a faster turnaround time compared to many manual methods. The automated method also works on a smaller issue sample than current methods. Specifically, the automated method can extract RNA from a single, four micron tissue section. Many on-market methods require ten micron tissue sections, or multiple four micron sections pooled in a single sample. Additionally, without wishing to limit the present invention to any theory or mechanism, the automated method may release RNA from the tissue without a lengthy protease treatment. Many manual methods treat with protease for multiple hours. The automated method uses a short protease treatment resulting in an RNA population that is far less degraded than the population of RNA extracted using manual methods. Less degradation likely indicates the presence of more full-length transcripts, which may benefit users interested in downstream applications such as sequencing or qPCR analysis.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Any reference numbers recited in the claims or specification are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

Any reference numbers recited in the claims or specification are solely for ease of examination of this patent application, and are exemplary, and are not intended in any way to limit the scope of the claims to the particular features having the corresponding reference numbers in the drawings.

What is claimed is:

1. An automated method for extracting nucleic acid from tissue samples disposed on one or more slides in an automated staining machine, wherein the method comprises the following steps:
   (a) treating the samples on the one or more slides with a deparaffinization reagent;
   (b) treating the samples on the one or more slides with an antigen retrieval buffer;
   (c) treating the samples on the one or more slides with a protease buffer; and
   (d) heating the samples on the one or more slides to yield an eluate,
   wherein the eluate comprises isolated nucleic acid from the respective sample, and
   wherein the samples on the one or more slides are stained samples.

2. The method of claim 1, further comprising removing the eluate from the samples on the one or more slides.

3. The method of claim 2, further comprising purifying the isolated nucleic acid.

4. The method of claim 2, further comprising performing nucleic acid amplification on the isolated nucleic acid.

5. The method of claim 3, further comprising analyzing the isolated nucleic acid.

6. The method of claim 5, wherein the analyzing comprises sequencing.

7. The method of claim 1, wherein the nucleic acid is DNA.

8. The method of claim 1, further comprising treating the samples on the one or more slides with guanidine thiocyanate after step (c).

9. The method of claim 8, wherein the nucleic acid is RNA.

10. The method of claim 1, wherein the samples on the one or more slides are FFPE samples, fresh samples, or frozen samples.

11. The method of claim 1, wherein the samples are microdissected samples.

12. The method of claim 1, wherein the stained samples are samples stained with haematoxylin and eosin (H&E), an immunohistochemistry dye, or an in situ hybridization dye.

13. The method of claim 1, wherein the automated staining machine comprises one or more dispensers for dispensing the deparaffinization reagent, antigen retrieval buffer, and protease onto the samples on the one or more slides.

14. The method of claim 13, wherein the automated staining machine further comprises a heating element for heating the samples on the one or more slides.

15. An automated method for extracting RNA from tissue samples disposed on one or more slides in an automated staining machine, wherein the method comprises the following steps:
   (a) treating the samples on the one or more slides with a deparaffinization reagent;
   (b) treating the samples on the one or more slides with an antigen retrieval buffer;
   (c) treating the samples on the one or more slides with a protease;
   (d) treating the samples on the one or more slides with guanidine thiocyanate; and
   (e) heating the samples on the one or more slides to yield an eluate,
   wherein the eluate comprises isolated nucleic acid from the respective sample, and
   wherein the one or more slides are stained samples.

16. The method of claim 15, further comprising removing the eluate from the samples on the one or more slides.

17. The method of claim 16, further comprising purifying the isolated nucleic acid.

18. The method of claim 17, further comprising performing nucleic acid amplification on the isolated nucleic acid.

19. The method of claim 18, further comprising analyzing the isolated nucleic acid.

20. The method of claim 19, wherein the analyzing comprises sequencing.

21. The method of claim 15, wherein the samples on the one or more slides are FFPE samples, fresh samples, or frozen samples.

22. The method of claim 15, wherein the samples are microdissected samples.

23. The method of claim 15, wherein the stained samples are samples stained with H&E or an immunohistochemistry dye or an in situ hybridization dye.

24. An automated method for extracting nucleic acid from tissue samples disposed on one or more slides, wherein the method comprises the following steps:
   (a) receiving the one or more slides comprising one or more tissue samples in an automated slide staining apparatus, wherein the one or more tissue samples are stained, wherein the automated slide staining apparatus is configured to automatically dispense a plurality of nucleic acid extraction reagents to the one or more tissue samples to treat the one or more tissue samples, respectively, the nucleic acid extraction reagents comprising a deparaffinization buffer, an antigen retrieval buffer, and a protease buffer;
   (b) dispensing said reagents in a predetermined sequence such that the reagents come into contact with the one or more tissue samples on the one or more slides; and
   (c) treating the one or more tissue samples on the one or more slides with the reagents, thereby resulting in one or more extracted nucleic acid samples comprising extracted nucleic acid.

25. The method of claim 24, further comprising heating the tissue samples to elute extracted nucleic acid from the tissue sample.

26. The method of claim 24, further comprising removing the one or more extracted nucleic acid samples from the one or more slides.

27. The method of claim 26, further comprising purifying the nucleic acid from one or more extracted nucleic acid samples.

28. The method of claim 27, further comprising analyzing the nucleic acid from one or more extracted nucleic acid samples.

29. The method of claim 28, wherein the analyzing comprises performing nucleic acid amplification.

30. The method of claim 28, wherein the analyzing comprises nucleic acid sequencing.

31. The method of claim 24, wherein the extracted nucleic acid is DNA.

32. The method of claim 24, wherein the reagents further comprise guanidine thiocyanate.

33. The method of claim 32, wherein the extracted nucleic acid is RNA.

34. The method of claim 24, wherein the one or more tissue samples are fresh, frozen, formalin fixed, or paraffin embedded.

35. A method for isolating nucleic acid from a sample on a slide, wherein the method comprises the following steps:
(a) placing the sample on the slide on an automated staining machine, wherein the sample is a stained sample;
(b) running an extraction protocol on the automated staining machine, wherein the extraction protocol instructs the automated staining machine to dispense reagents, wherein the reagents comprise: (i) a deparaffinization buffer, (ii) an antigen retrieval buffer, (iii) and a protease buffer, wherein the reagents are dispensed on the slide in a predetermined sequence, such that said reagents come into contact with the sample on the slide, thereby resulting in an eluate on the sample on the slide, and wherein the eluate comprises an isolated nucleic acid sample comprising isolated nucleic acid.

36. The method of claim 35, further comprising heating the sample to yield the eluate on the sample on the slide.

37. The method of claim 35, further comprising removing the eluate on the sample on the slide.

38. The method of claim 37, further comprising purifying the isolated nucleic acid.

39. The method of claim 38, further comprising performing nucleic acid amplification on the isolated nucleic acid.

40. The method of claim 37, further comprising analyzing the isolated nucleic acid.

41. The method of claim 40, wherein the analyzing comprises sequencing.

42. The method of claim 35, wherein the nucleic acid is DNA or RNA.

43. The method of claim 35, wherein the reagents further comprise guanidine thiocyanate.

44. The method of claim 35, wherein the samples are FFPE samples, fresh samples, or frozen samples.

45. The method of claim 35, wherein the samples are samples stained with H&E or an immunohistochemistry dye or an in situ hybridization dye.

46. A method for isolating nucleic acid from a sample on a slide, wherein the method comprises the following steps:
(a) placing the sample on the slide on a dissection instrument, wherein the sample is a stained sample;
(b) dissecting the sample on the slide to remove unwanted tissue;
(c) placing the sample on the slide on an automated staining machine; and
(d) running an extraction protocol on the automated staining machine, wherein the extraction protocol instructs the automated staining machine to dispense reagents, wherein the reagents comprise: (i) a deparaffinization buffer, (ii) an antigen retrieval buffer, and (iii) a protease buffer, wherein the reagents are dispensed on the slide in a predetermined sequence, such that said reagents come into contact with the sample on the slide, thereby resulting in an eluate on the sample on the slide, and wherein the eluate comprises an isolated nucleic acid sample comprising isolated nucleic acid.

47. The method of claim 46, further comprising heating the sample to yield the eluate on the sample on the slide.

48. The method of claim 46, further comprising removing the eluate on the sample on the slide.

49. The method of claim 48, further comprising purifying the isolated nucleic acid.

50. The method of claim 49, further comprising performing nucleic acid amplification on the isolated nucleic acid.

51. The method of claim 50, further comprising analyzing the isolated nucleic acid.

52. The method of claim 51, wherein the analyzing comprises sequencing.

53. The method of claim 46, wherein the nucleic acid is DNA or RNA.

54. The method of claim 46, wherein the reagents include guanidine thiocyanate.

55. The method of claim 46, wherein the samples are FFPE samples, fresh samples, or frozen samples.

56. The method of claim 46, wherein the stained samples are samples stained with H&E or an immunohistochemistry dye or an in situ hybridization dye.

57. A workflow method, wherein the workflow method comprises: preparing a tissue section from a tissue of a patient on a slide; applying the method according to claim 1 to the tissue section on the slide, wherein the method is for extracting nucleic acid.

58. The workflow method of claim 57, wherein the tissue of the patient is a tumor tissue.

59. A workflow method, wherein the workflow method comprises the following steps:
(a) sectioning a formalin-fixed paraffin-embedded (FFPE) tissue section from a tumor of a patient;
(b) mounting the tissue section on a slide; and
(c) applying a method according to claim 1 to the tissue section in an automated machine that automatically dispenses a plurality of nucleic acid extraction reagents to the tissue section on the slide, thereby resulting in an extracted nucleic acid sample comprising extracted nucleic acid derived from the tissue section.

* * * * *